United States Patent
Lee et al.

(10) Patent No.: US 8,298,128 B2
(45) Date of Patent: Oct. 30, 2012

(54) CENTRIFUGE SEPARATING FLUIDS BY ADJUSTING ROTATION SPEED USING ROTATOR AND CENTRIFUGING METHOD OF THE SAME

(75) Inventors: Hee-Young Lee, Gunsan (KR); Jun-Seok Lee, Nam-gu Busan (KR)

(73) Assignee: Medikan Inc., Seoul (KR)

( * ) Notice: Subject to any disclaimer, the term of this patent is extended or adjusted under 35 U.S.C. 154(b) by 549 days.

(21) Appl. No.: 12/307,124

(22) PCT Filed: Jan. 3, 2007

(86) PCT No.: PCT/KR2007/000020
§ 371 (c)(1),
(2), (4) Date: Feb. 20, 2009

(87) PCT Pub. No.: WO2008/001992
PCT Pub. Date: Jan. 3, 2008

(65) Prior Publication Data
US 2010/0069215 A1     Mar. 18, 2010

(30) Foreign Application Priority Data

Jun. 30, 2006 (KR) .................. 10-2006-0060512
Nov. 10, 2006 (KR) .................. 10-2006-0111266

(51) Int. Cl.
*B04B 5/02* (2006.01)
(52) U.S. Cl. .................. 494/7; 494/20; 494/27; 494/37; 494/56
(58) Field of Classification Search .............. 494/11–12, 494/16, 20, 45, 63, 31, 33, 37, 43, 56, 7–9, 494/23–30
See application file for complete search history.

(56) References Cited

U.S. PATENT DOCUMENTS

| 717,385 | A | * | 12/1902 | Gathmann | 494/33 |
|---|---|---|---|---|---|
| 2,710,718 | A | * | 6/1955 | Denman | 494/27 |
| 3,190,547 | A | * | 6/1965 | Shanley | 494/11 |
| 5,217,426 | A | | 6/1993 | Bacehowski et al. | |
| 5,707,331 | A | * | 1/1998 | Wells et al. | 494/20 |
| 5,899,349 | A | | 5/1999 | Moore | |
| 6,132,353 | A | * | 10/2000 | Winkelman et al. | 494/16 |
| 6,398,705 | B1 | * | 6/2002 | Grumberg et al. | 494/16 |
| 6,689,042 | B2 | | 2/2004 | Unger et al. | |
| 6,773,389 | B2 | | 8/2004 | Hlavinka et al. | |
| 2010/0069215 | A1 | * | 3/2010 | Lee et al. | 494/7 |

FOREIGN PATENT DOCUMENTS

| WO | 2008/002004 A1 | * | 1/2008 |
| WO | 2008/002094 A1 | * | 1/2008 |
| WO | WO 2008/001992 A1 | | 1/2008 |

* cited by examiner

*Primary Examiner* — Charles E Cooley
(74) *Attorney, Agent, or Firm* — Ladas & Parry LLP

(57) ABSTRACT

A centrifuge includes a rotator comprising a receiving unit receiving materials and guiding the materials to move upward by centrifugal force to an upper portion of the receiving unit, and a rotator cover covering the upper portion of the receiving unit. The centrifuge also includes a container that is coupled to the rotator cover to be connected to the receiving unit and that receives the materials moved upward along the receiving unit. The centrifuge and a centrifuging method as disclosed herein are used for separating a fluid to which a large centrifugal force is applied and a fluid to which a smaller centrifugal force is applied by adjusting the rotation speed using the principle that centrifugal force during rotation varies according to specific components of a fluid. Thus, using the centrifuge and the centrifugal method, materials can be centrifuged and layers of the materials can be classified and collected accurately and easily.

20 Claims, 15 Drawing Sheets

CENTRIFUGE SEPARATING FLUIDS BY ADJUSTING ROTATION SPEED USING ROTATOR AND CENTRIFUGING METHOD OF THE SAME

CROSS-REFERENCE TO RELATED PATENT APPLICATION

This application is a national phase of International Application No. PCT/KR2007/000020, entitled "CENTRIFUGE AND CENTRIFUGING METHOD", which was filed on Jan. 3, 2007, and which claims priority of Korean Patent Application No. 10-2006-0060512, filed on Jun. 30, 2006 and Korean Patent Application No. 10-2006-0111266, filed on Nov. 10, 2006, respectively, in the Korean Intellectual Property Office, the disclosure of which is incorporated herein in its entirety by reference.

BACKGROUND OF THE INVENTION

1. Technical Field

The present invention relates to a centrifuge and a centrifuging method of separating a fluid to which a large centrifugal force is applied and a fluid to which a smaller centrifugal force is applied by adjusting the rotation speed using the principle that centrifugal force during rotation varies according to specific components of a fluid. Thus, using the centrifuge and the centrifugal method, materials can be centrifuged and layers of the materials can be classified and collected accurately and easily.

2. Background Art

The centrifuge and the centrifugal method according to the present invention can be applied to any material that can move in a downward direction on a surface slanted against the direction of gravity such as liquid, powder, gel, mixture of liquid and solid, colloid, solids having a form near to spheres, etc.

A centrifuge is an apparatus for separating materials using centrifugal force that is generated when an object is rotated. The centrifuge can be classified according to the amount of a sample to be centrifuged, the rotation speed, the rotor, etc.

A centrifuge is used in biotechnology to separate cells mixed in a liquid or a material having greater weight and adhesive force than a liquid. Recently, intensive research on adult stem cells has been conducted, and a centrifugal method of separating a small amount of stem cells from a large amount of adult tissues (fat, bone-marrow, etc.) is currently being researched.

As a centrifuge used in biotechnology is required to separate human body cells without destroying them, a smaller centrifugal force is used for separating human body cells than when separating a general material. The centrifugal force required for centrifuging of cells is 100 G maximum, usually lower than this. Here, G denotes a gravitational constant. Since a centrifugal force is exerted as gravity in a centrifuge, a centrifugal force will be represented using the unit 'G'.

When a complex fluid such as blood is centrifuged using a centrifuge in biotechnology laboratory, the fluid is divided into several layers according to the specific gravity of each element of the complex fluid. Here, a complex fluid refers to a liquid that includes semisolids such as fine solid components or gel and has a broader range than a polymer; hereinafter, it will be referred to as 'fluid'.

Technical Problem

When a cell is separated using a centrifuge, each centrifuged layer of fluid is stacked in a test tube and can be discriminated visually; however, it is difficult to separate the layers physically. Layers of a fluid centrifuged by a centrifuge are generally separated by hand. However, separating layers of a centrifuged fluid is an onerous task, and moreover, loss of the centrifuged material may be caused and thus purity of the separated material cannot be secured.

A liquid of an upper layer right above the cell mostly consists of water, and when the test tube is slowly inclined to pour out the liquid from the tube, the cell in a bottom layer flows together with the upper layer and thus the cell centrifuged by the centrifuge may be swept away.

Without a centrifugal force, the cohesive or adhesive force between cells is not distinctively different from that of water, and thus over 50% of pouring out of the liquid from the tube fails. Even when the pouring out is successful, some of the cells in the top layer may be swept away. If a centrifugal force is increased to stick the cells to each other, the cells may be destroyed.

Thus the testers have proposed been using a pipette to remove the upper layer using a pipette. However, a portion of the liquid to be removed still remains in the tube and thus at least seven or eight dilution processes need to be performed.

For example, when stem cells are separated from fat tissues, classifying a minimum amount of stem cells by solving a large amount of tissues using a solvent such as collagen and washing the centrifuged material are performed. The separated material is washed for removing unnecessary medical elements and other elements included in the material to use the separated material again in the human body. However, washing requires a lot of time and may destroy the stem cells. In other words, in the washing process, the centrifuged material is manipulated several times, and thus the time the stem cell is exposed to the air is prolonged, thereby increasing the risk of contamination of the stem cells.

Technical Solution

The present invention provides a centrifuge and a centrifugal method in which a material is separated by a centrifugal force and layers of the centrifuged material are separated accurately and can be easily collected.

The present invention also provides a centrifuge and a centrifugal method in which stem cells are accurately classified and collected from layers of a material centrifuged by the centrifuge.

According to an aspect of the present invention, there is provided a centrifuging method and a centrifuge separating a fluid to which a large centrifugal force is applied and a fluid to which a smaller centrifugal force is applied by adjusting the rotation speed using the principle that the centrifugal force during rotation varies according to the specific component of a fluid.

The centrifuge and the centrifuging method according to the present invention is for centrifuging a complex fluid (a liquid that includes semisolids such as fine solid components or gel and has a broader range than a polymer; hereinafter referred to as 'fluid') such as blood extracted from a human body, fat, and the like. In detail, according to the present invention, stem cells contained in a small amount in a complex fluid such as fat extracted from a human body can be centrifuged, and the stem cells moved by the operation of centrifugal force is accumulated in a container that is detachably installed, and thus the stem cells can be accurately and easily collected without any additional separation process or washing process.

The centrifuge and the centrifuging method according to an embodiment of the present invention can be applied to all kinds of materials that can move downward from an inclined surface forming an inclination with respect to gravity, that is, both to liquids and solids such as liquid, powder, gel, a mixture of liquid and solid, colloid, solids that are nearly spherical.

According to an aspect of the present invention, there is provided a centrifuge comprising: a rotator comprising a receiving unit receiving materials and guiding the materials to move upward by centrifugal force to an upper portion of the receiving unit, and a rotator cover covering the upper portion of the receiving unit; and a container that is coupled to the rotator cover to be connected to the receiving unit and that receives the materials moved upward along the receiving unit.

The receiving unit may comprise a vertical guiding portion whose horizontal cross-section becomes reduced downwardly such that the materials received in the receiving unit flow upward by centrifugal force.

The receiving unit may further comprise a horizontal guiding portion that is inclined upward from an upper end of the vertical guiding portion and extended to the outside, and the horizontal guiding portion comprises at least one convergent portion where the centrifugal force is maximal such that the materials moved upward from the vertical guiding portion move along an inner wall of the horizontal guiding portion and converge into the convergent portion by centrifugal force.

Using the centrifuge according to the present invention including a receiving unit having a cross-section increasing upwardly, the material flows from the bottom of the receiving unit upward by the centrifugal force. The segregated layers are arranged such that the layers applied by a larger centrifugal force are stacked in outer position of the container.

When the rotation is being continued at a reduced rotation speed after segregation of layers is completed, gravity and centrifugal force exerted on each layer vary according to the fluid dynamic characteristic of each of the segregated layers. Some layers to which relatively larger gravity is applied flow down to the bottom of the receiving unit, and some layers to which relatively larger centrifugal force is applied remain in the container.

Thus the present invention provides a centrifuge and a centrifuging method using the centrifuge that can accurately separate and collect layers of stem cells in the centrifuge without any additional separation or washing process based on the characteristic of stem cells in a complex fluid such as fat tissue extracted from a human body, which has larger fluid resistance compared to other elements contained in a fluid of fatty tissue and is affected by a relatively larger centrifugal force at the same rotation speed than other materials.

A horizontal cross-section of the horizontal guiding portion may be formed of two arcs that are coupled together to be curved outwardly.

The vertical guiding portion may be formed of an inverted conical shape.

The inner wall of the vertical guiding portion may be curved inwardly.

A surface of the receiving unit may be coated to reduce surface resistance against the flow of the materials.

The rotator cover may comprise a stopper portion that is connected to the receiving unit and opened to an upper portion of the rotator cover, and the container may be rotatably coupled to the stopper portion, and the container may be rotated between a coupled state, in which an opening of the container faces the stopper portion and is connected to the receiving unit, and a release state, in which the opening of the container is detached from the stopper portion.

The stopper portion may be disposed to correspond to the convergent portion of the horizontal guiding portion.

The stopper portion may support the container such that the angle of the center axis of the container with respect to the rotation axis of the rotator is maintained above 90 degrees and below 180 degrees.

The stopper portion may comprise a supporting portion supporting the container in a coupled state by applying a magnetic force to the container. After a portion of the centrifuged material has flown down to the receiving unit with a reduced rotation speed of the rotator, the container may be converted into the release state by the supporting portion exerting opposite magnetic force or releasing magnetic force, and the container may be rotated downward by gravity and centrifugal force so that the angle of the center axis of the container with respect to the rotation axis of the rotator is less than 90 degrees.

A coupling piece and a locking device which is operated by external signals to be coupled to the coupling piece and supports the container in the coupled state, may be installed between the stopper portion and the container. After a portion of the centrifuged material has flown down to the receiving unit with a reduced rotation speed of the rotator, the container may be converted into the release state by releasing the coupling of the locking device to the coupling piece, and the container may be rotated downward by gravity and centrifugal force so that the angle of the center axis of the container with respect to the rotation axis of the rotator may be less than 90 degrees.

The container may be rotatably coupled to the stopper portion by a pivot axis disposed therebetween, and the pivot axis is driven by a forceful driving unit operated by external signals.

The centrifuge may further comprise a case surrounding the rotator, and a first magnetic body is installed in the case, and a second magnetic body is installed in an outer portion of the rotator, and while the rotator is rotated, the rotator and the case are maintained at a predetermined distance from each other by repulsive force between the first magnetic body and the second magnetic body.

The centrifuge may further comprise: a case cover that is coupled to the case to cover the upper portion of the rotator; and an inflow tube that passes through the case cover and the rotator cover from the outside and is inserted into the receiving unit of the rotator, and that discharges the material received in the receiving unit to the outside or injects an external material into the receiving unit.

The centrifuge according to the present invention is rotated at a maximum speed required for centrifuging, that is, at a first speed for a predetermined period of time to centrifuge a material into segregated layers, and then slowed down to a second speed that is lower than the first speed and is rotated again for a predetermined period of time. The second speed is determined by the characteristic of the material to be centrifuged, and particularly, by the fluid resistance. When the rotator is continuously being rotated at the reduced rotation speed, that is, at the second speed, some of segregated layers formed in the container and over the receiving unit of the rotator are affected by a centrifugal force that is greater than gravity and thus remain inside the container; however, the other segregated layers may flow down to the bottom of the receiving unit affected by a centrifugal force that is smaller than gravity. As described above, according to the present invention, the second speed is adjusted according to the segregated layers to be centrifuged to determine a critical point at which some segregated layers can flow down to the bottom of the receiving unit.

According to another aspect of the present invention, there is provided a method of centrifuging using a rotator comprising: a receiving unit guiding a material to move upward by centrifugal force; a rotator cover covering an upper portion of the receiving unit; and a container that is detachably coupled to the rotator cover and connected to the receiving unit, the method comprising: supplying a material to the receiving unit; (b) centrifuging the material by rotating the rotator at a first speed such that the material moves to an upper portion of the receiving unit and flows into the container; (c) reducing the rotation speed of the rotator to a second speed that is lower than the first speed such that some layers of the centrifuged material flow down into to the receiving unit; (d) decoupling the container from the rotator cover such that an opening of the container is directed upward; and (e) stopping the rotator.

Operation (c) may further comprise discharging the material received in the receiving unit using the inflow tube that passes through the rotator cover and is connected into the receiving unit of the rotator, after the rotation speed of the rotator is reduced to the second speed.

The method may further comprise injecting a washing solution into the receiving unit through the inflow tube after discharging the material received in the receiving unit, and repeating (b) and (c).

The second speed may be set as a speed creating a centrifugal force which facilitates to attach an outermost layer, which is segregated by centrifuge, to the container and makes the other layers flow down to the receiving unit by gravity.

The second speed may be set whereby 1 through 80 G of centrifugal force is applied to the material.

Advantageous Effects

As described above, according to the centrifuge and the centrifugal method, a material can be centrifuged and layers of the centrifuged material can be accurately and easily classified and collected.

Also, in the centrifuge and the centrifugal method according to the present invention, stem cells moved from the inside of the centrifuge upward and are collected in a container with the effect of a centrifugal force, and thus stem cells can be accurately classified and collected without additional classifying or washing process.

The present invention will now be described more fully with reference to the accompanying drawings, in which exemplary embodiments of the invention are shown.

Figure 1:
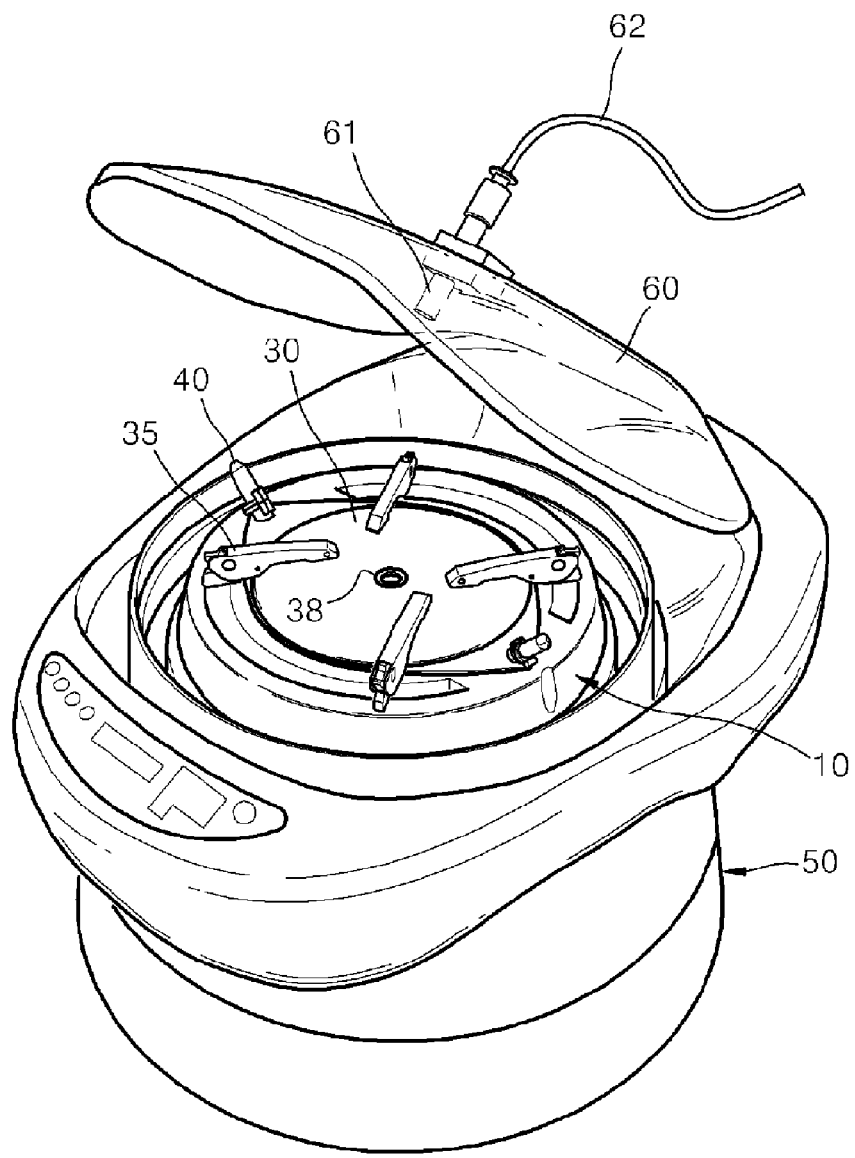
FIG. 1 is a perspective view illustrating a centrifuge according to an embodiment of the present invention.
Figure 2:
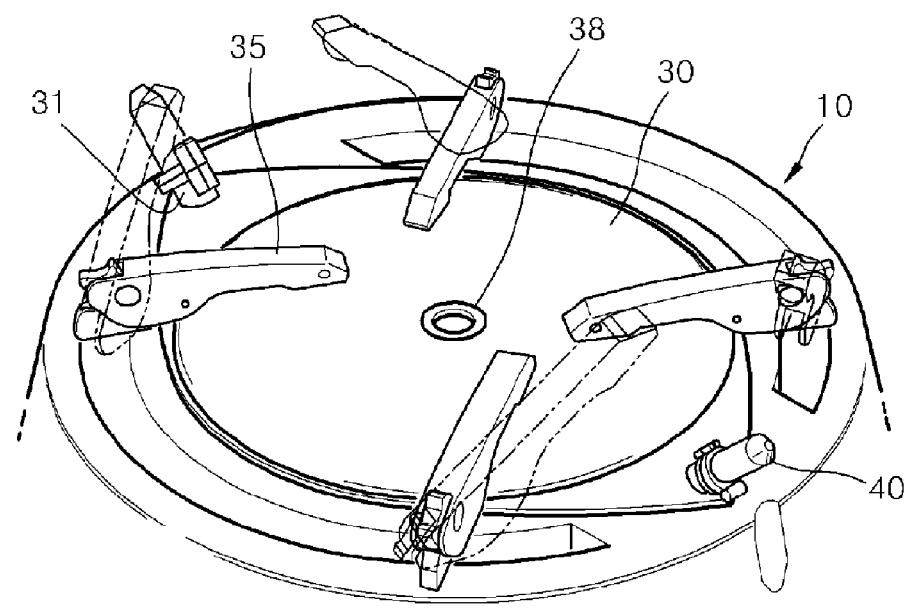
FIG. 2 is a partial perspective view illustrating an upper portion of the centrifuge of FIG. 1, according to an embodiment of the present invention.

FIG. 1 is a perspective view illustrating a centrifuge according to an embodiment of the present invention; FIG. 2 is a partial perspective view illustrating an upper portion of the centrifuge of FIG. 1; and FIG. 3 is a side cross-sectional view illustrating the centrifuge of FIG. 1.

Figure 3:
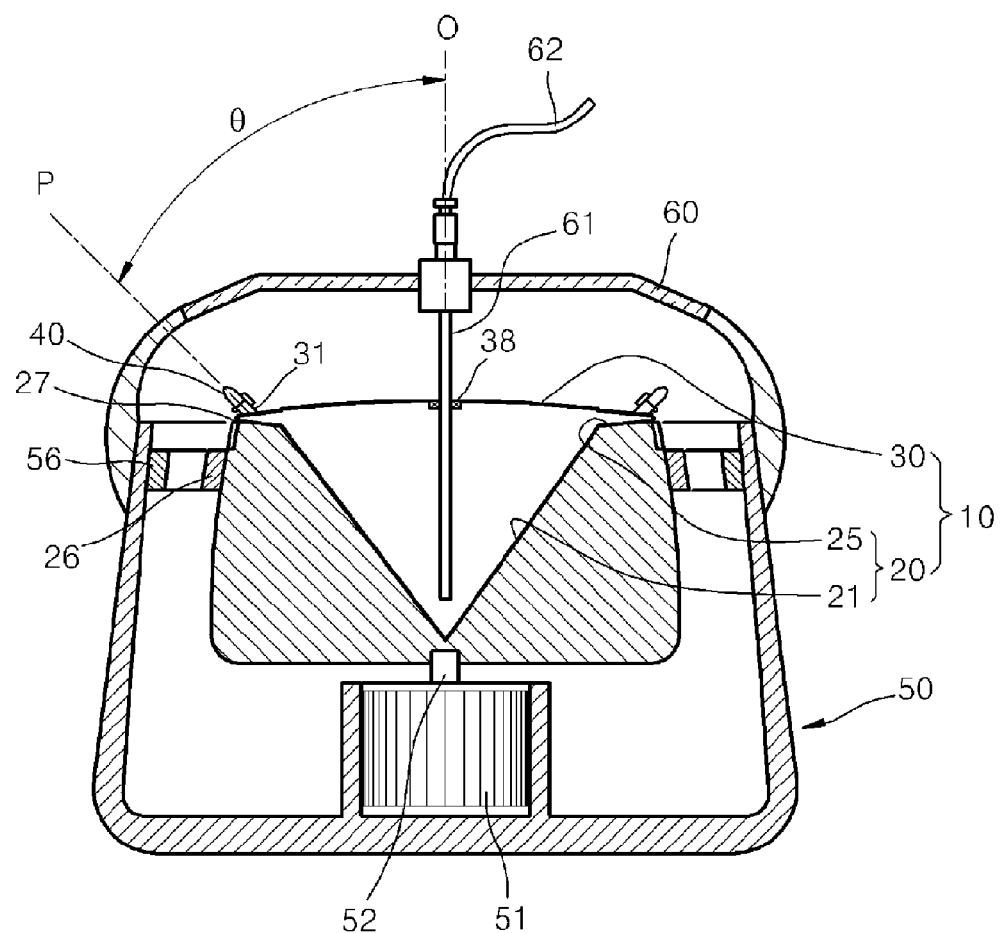
FIG. 3 is a side cross-sectional view illustrating the centrifuge of FIG. 1, according to an embodiment of the present invention.

The centrifuge illustrated in FIGS. 1 through 3 can separate a material by a centrifugal force, and moreover, can accurately and easily classify and collect partial layers from the centrifuged material, for example, just stem cells can be separated and collected from the centrifuged material. Referring to FIGS. 1 through 3, the centrifuge according to the current embodiment of the present invention includes a rotator 10 rotating around a rotation axis 0 and a container 40 that is coupled to the rotator 10.

The rotator 10 of the centrifuge receives a material that is to be centrifuged inside of the rotator 10 and is rotated around the rotation axis 0. The material is received in a receiving unit 20 that is formed inside the rotator 10. The receiving unit 20 guides the material to move in an upward direction of the rotator 10 by a centrifugal force. The rotator 10 includes a rotator cover 30 covering the upper portion of the receiving unit 20.

The rotator cover 30 is coupled to the upper portion of the receiving unit 20, and while the rotator 10 is rotating, the rotator cover 30 seals the receiving unit 20 and guides the flow of the material. Accordingly, the rotator cover 30 is formed in a shape corresponding to an upper opening of the receiving unit 20. The rotator cover 30 is coupled to the container 40. The opening of the container 40 is connected with the receiving unit 20. Accordingly, the material moved to the upper portion of the receiving unit 20 by a centrifugal force can flow into the inside of the container 40.

A plurality of clips 35 are mounted around the rotator cover 30 on the upper surface of the rotator 10. The clips 35 apply a downward pressure to the rotator cover 30, and thus closely couple the rotator cover 30 to the rotator 10.

A material received in the receiving unit 20 may be a fluid such as blood extracted from the human body. When the fluid is centrifuged by the rotation of the rotator 10, the fluid is segregated into various layers such as fat, free oil, water, stem cells, etc., and the stem cells which move from the receiving unit 20 outward and flow into the container 40.

The centrifuge further includes a case 50 surrounding the rotator 10. A first magnetic body 56 is installed on an inner surface of the case 50, and a second magnetic body 26 is installed on an outer surface of the rotator 10. The first magnetic body 56 is ring-shaped, extending along the inner circumference of the case 50, and the second magnetic body 26 may also be ring-shaped, extending along the outer circumference of the rotator 10. The first magnetic body 56 and the second magnetic body 26 face each other, and surfaces thereof are formed of permanent magnets having the same polarity, and thus a repulsive force can be exerted between the first magnetic body 56 and the second magnetic body 26.

According to the first and second magnetic bodies 56 and 26, even when the rotator 10 is rotated at high speed, since the first and second magnetic bodies 56 and 26 exert a repulsive force therebetween, the rotator 10 and the case 50 can be retained with a pre-determined distance between them. Accordingly, the rotator 10 can be rotated continuously and stably, without shaking.

The rotator 10 is accommodated in the case 50, and a case cover 60 is coupled to the case 50 to cover the upper portion of the rotator 10.

An inflow tube 61 is connected with the case cover 60. The inflow tube 61 passes through the case cover 60 and the rotator cover 30 and is inserted into the inside of the rotator 10. An end portion of the inflow tube 61 is opened in the receiving unit 20. Although not illustrated in the drawings, the inflow tube 61 is formed like a telescope such that the length of the inflow tube 61 can expand and contract. The inflow tube 61 is connected to a hose 62 coupled to the upper portion of the case cover 60. Accordingly, the inflow tube 61 is inserted into the inside of the rotator 10 so as to inject external material into the inside of the rotator 10 or to discharge material inside the rotator 10 to the outside.

While the rotator 10 is rotated, interference between the inflow tube 61 and the rotator cover 30 should not occur, and moreover, material in the receiving unit 20 should not be discharged. Thus the inflow tube 61 can pass through a bearing 38 installed in a through hole formed in the center of the rotator cover 30 and be inserted into the inside of the receiving unit 20. Also, a ring-shaped sealing (not shown) may be installed in the through hole formed in the center of the rotator cover 30.

Accordingly, the bearing 38 supports the inflow tube 61 so that interference may not occur between the inflow tube 61 and the rotator cover 30 during the rotation of the rotator 10 and, in addition, seal the receiving unit 20.

The rotator 10 can be rotated using various rotating methods. In the current embodiment of the present invention, the rotator 10 is rotated by a driving motor 51 The rotator 10 is coupled to a driving axis 52 of the driving motor 51, and thus is rotated around the driving axis 52.

Figure 4:
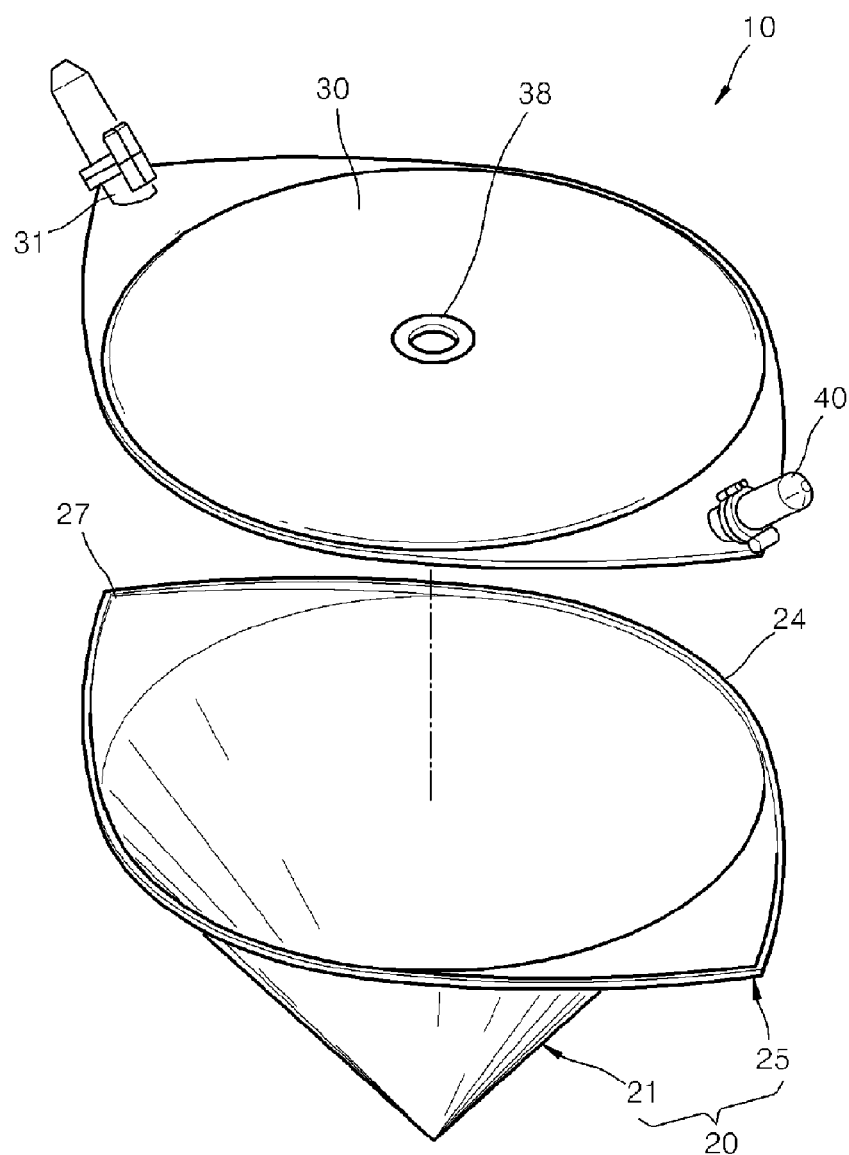
FIG. 4 is a perspective view illustrating a rotator of the centrifuge of FIG. 1, according to an embodiment of the present invention.
Figure 5:
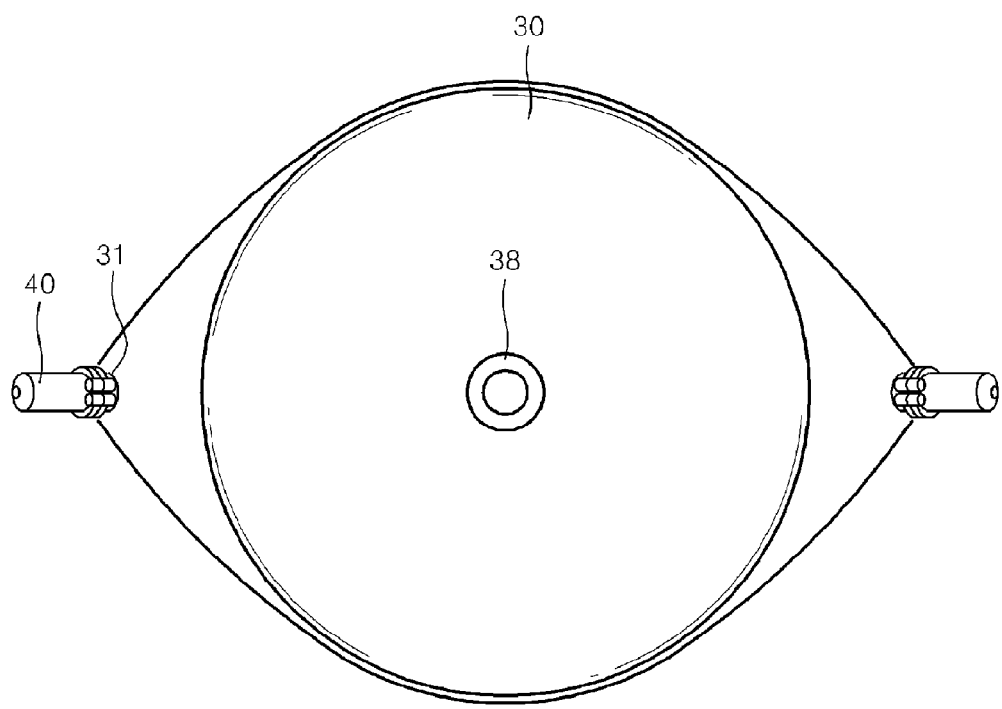
FIG. 5 is a plan view illustrating a rotator cover of the rotator of FIG. 4, according to an embodiment of the present invention.

FIG. 4 is a perspective view illustrating the rotator of the centrifuge of FIG. 1; FIG. 5 is a plan view illustrating the rotator cover 30 of the rotator 10 of FIG. 4; and FIG. 6 is a side cross-sectional view illustrating the layers of the centrifuged material in the rotator of the centrifuge illustrated in FIG. 1, according to an embodiment of the present invention.

Figure 6:
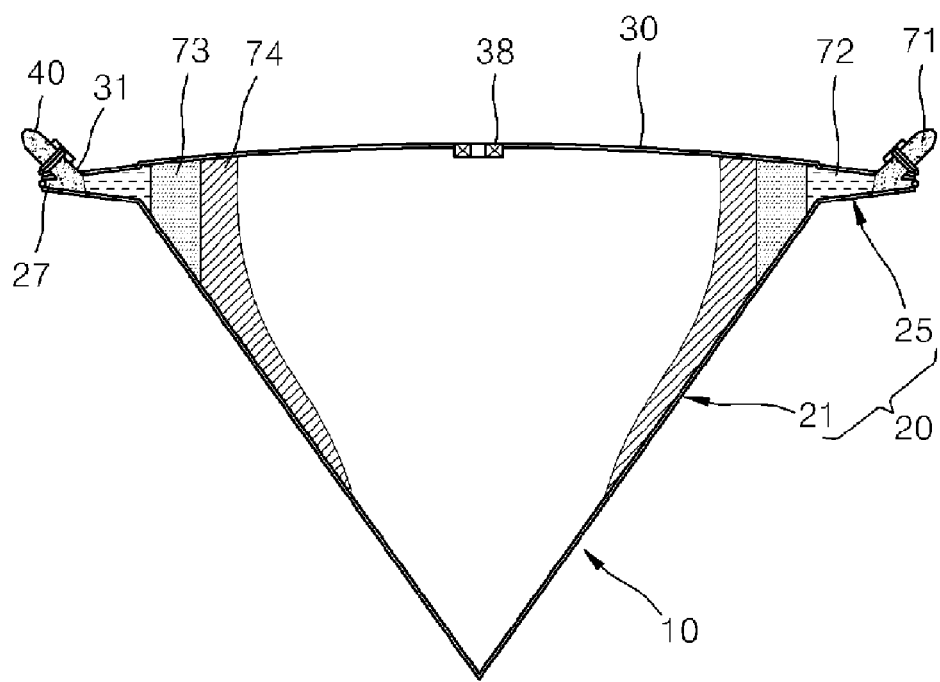
FIG. 6 is a side cross-sectional view illustrating the layers of the centrifuged material in the rotator of the centrifuge illustrated in FIG. 1, according to an embodiment of the present invention.

Referring to FIGS. 4 through 6, the receiving unit 20 includes a vertical guiding portion 21 having an inverted conical shape such that the material received in the receiving unit 20 flows to the upper portion of the receiving unit 20 due to a centrifugal force. Also, the receiving unit 20 includes a horizontal guiding portion 25 which is inclined upward from an upper end of the vertical guiding portion 21 and is extended outward.

The vertical guiding portion 21 guides the material to move upward due to a centrifugal force during the rotation of the rotator 10. The vertical guiding portion 21 has an inverted conical shape, and thus the inner wall of the vertical guiding portion 21 is inclined with respect to the direction of gravity. (Hereinafter, an inclined surface formed by the inner wall of the vertical guiding portion 21 will be referred to as a 'gravity inclined surface). The gravity inclined surface guides the flow of the material upward when a centrifugal force is applied to the material by the rotation of the rotator 10. In other words, when a centrifugal force exerted on the fluid is increased by the rotation of the rotator 10, the fluid overcomes gravity and may flow upward along the gravity inclined surface.

In the current embodiment of the present invention, a vertical cross-section of the vertical guiding portion 21 is triangular-shaped and thus the gravity inclined surface is formed straight by an oblique side of an inverted triangle. However, the sides of the vertical guiding portion 21 of the centrifuge according to the current embodiment of the present invention are not limited thereto, and may be curved inward or outward.

In the current embodiment of the present invention, the vertical guiding portion 21 has an inverted conical shape. Accordingly, a horizontal cross-section of the vertical guiding portion 21 is a circle. The reason that the vertical guiding portion 21 is formed as a cone is to prevent shaking of the rotator 10 due to the imbalance of the weight around the rotation axis to the right and left as much as possible when the rotator 10 is rotated at high speed. However, the shape of the vertical guiding portion 21 of the centrifuge according to the current embodiment of the present invention is not limited to a cone but may be any shape as long as the horizontal cross-section of the vertical guiding portion 21 gets smaller in a downward direction.

The horizontal guiding portion 25 is extended upward and outward from the vertical guiding portion 21, and guides the flow of the material in a horizontal direction at an upper end of the receiving unit 20. The horizontal guiding portion 25 may include at least one convergent portion 27 at a point of a horizontal cross-section where centrifugal force is maximal.

A horizontal cross-section at an upper end of the horizontal guiding portion 25 in the current embodiment is formed of two arcs coupled together, each being convex outwardly. Accordingly, a convergent portion 27 is formed at both ends of the horizontal guiding portion 25 where the two arcs meet. The convergent portion 27 is positioned at a farthest point where the two arcs meet from the center of the receiving unit 20 in a direction to the outer side, and thus corresponds to a point where a centrifugal force is maximal.

When the rotator 10 is rotated, a centrifugal force is exerted on the material in the vertical guiding portion 21, and thus the material moves along the gravity inclined surface to the upper portion of the of the receiving unit 20. The material passes by the upper end of the vertical guiding portion 21 and moves along the inner wall of the horizontal guiding portion 25 by the centrifugal force and gathers at the convergent portion 27. Accordingly, the inner inclined surface of the horizontal cross-section of the horizontal guiding portion 25 induces the flow of the material in a horizontal direction. Thus, an inner inclined surface of the horizontal guiding portion 25 will be referred to as a 'centrifugal force inclined surface 24' hereinafter.

In order to minimize the surface resistance which is caused by an inner wall surface of the receiving unit 20 when the material moves, the surface of the receiving unit 20 can be coated with a fluorine resin such as Teflon. Accordingly, when a centrifugal force is exerted on the material receiving unit 20, the material is guided by a gravity inclined surface and a centrifugal force inclined surface so as to easily move to the upper portion of the receiving unit 20.

Figure 7:
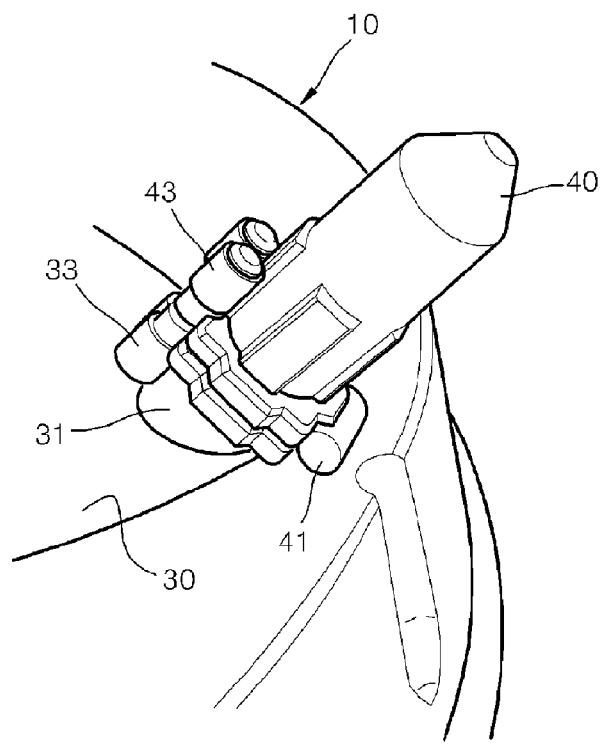
FIG. 7 is a partial perspective view illustrating a container mounted in the centrifuge of FIG. 1, according to an embodiment of the present invention.
Figure 8:
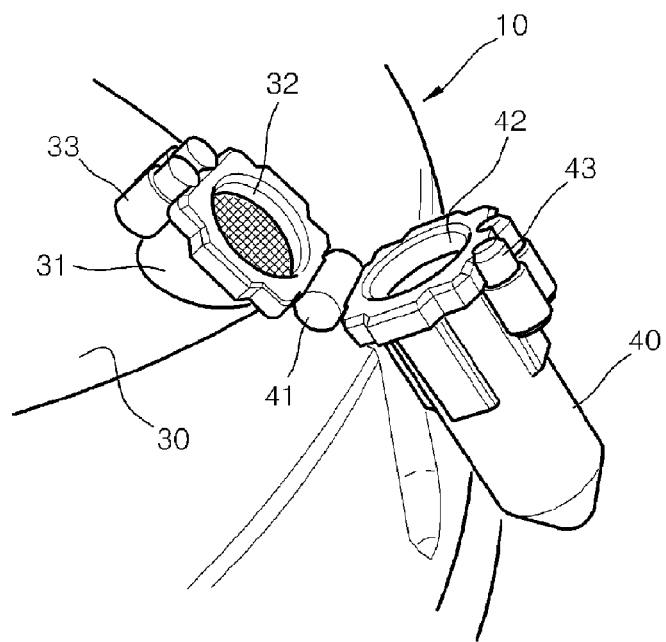
FIG. 8 is a partial perspective view illustrating the container illustrated in FIG. 7 when rotating, according to an embodiment of the present invention.
Figure 9:
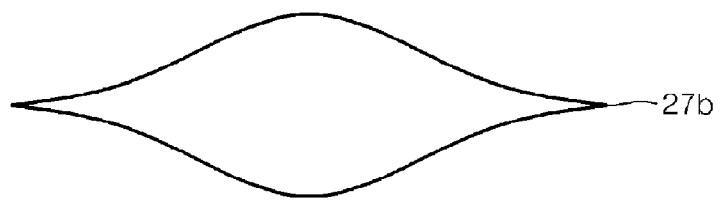
FIGS. 9 through 13 are cross-sectional views illustrating variations of horizontal cross-sections of a horizontal guiding portion of a centrifuge of FIG. 4 according to an embodiment of the present invention.
Figure 10:
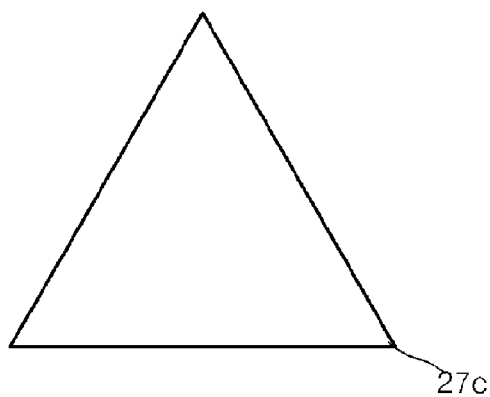
Figure 11:
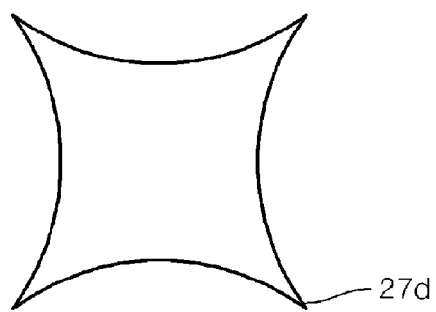
Figure 12:
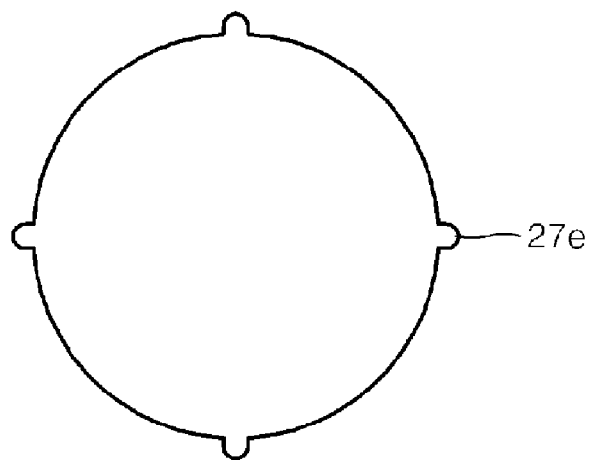
Figure 13:
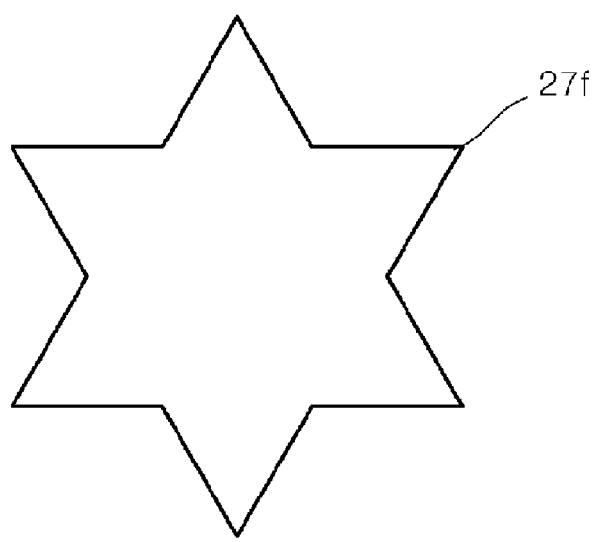

FIG. 7 is a partial perspective view illustrating the container 40 mounted in the centrifuge of FIG. 1; and FIG. 8 is a partial perspective view illustrating the container 40 when rotating, according to embodiments of the present invention.

A stopper portion 31 supporting the container 40 is installed at an upper portion of the rotator cover 30. The stopper portion 31 is disposed in a corresponding position to the convergent portion 27 of the rotator cover 30. The stopper portion 31 is connected to the receiving unit 20 and includes an outlet 32 that is opened to the upper portion of the rotator cover 30. Accordingly, when the container 40 is coupled to the stopper portion 31, the container 40 is connected to the receiving unit 20 through the stopper portion 31.

The container 40 is rotatably coupled to the stopper portion 31 by a pivot axis 41. The stopper portion 31 supports the container 40 to maintain a rotation angle 0 of a center axis P of the container 40 with respect to a rotation axis 0 within a range of over 90 degrees and below 180 degrees. In FIG. 3, the rotation angle 0 is illustrated to be from an upper portion of the rotation axis 0 to the center axis P of the container 40 for simplicity; however, to correspond to the description above, the rotation angle 0 is determined based on a reference angle 0, where the center axis P of the container 40 is parallel to the rotation axis 0 in a downward direction.

The container 40 is rotatably coupled to the stopper portion 31, and is also separable from the stopper portion 31. Since the container 40 can be separated from the stopper portion 31, stem cells can be collected simply by separating the container 40 from the rotator cover 30 after a centrifuging operation is completed.

When the container 40 is supported by the stopper portion 31, an opening 42 of the container 40 and an outlet 32 of the stopper portion 31 face each other, and thus the material of the receiving unit 20 can flow into the container 40. Such state is denoted as a 'coupled state'.

A supporting portion 33 supporting the container 40 fixedly in the stopper portion 31 is installed between the stopper portion 31 and the container 40. The supporting portion 33 comprises an electromagnet and applies a magnetic force to fixing pins 43 which are formed of metal or electromagnets, thus supporting the container 40 in a coupled state.

When the supporting portion 33 stops applying the magnetic force, the container 40 and the rotator cover 30 are decoupled, the container 40 is rotated around a pivot axis 41 due to the gravity of the container 40 and is moved to a 'release state' directed downward. Otherwise, the supporting portion 33 may exert a magnetic force opposite in polarity to that of the fixing pins 43 formed of a permanent magnet to rotate the container in a release state. In the release state, the opening of the container 40 is directed upward, and the material in the container 40 cannot flow out.

The operation of the centrifuge described above will be described hereinafter.

A material to be centrifuged is injected into the receiving unit 20 of the rotator 10. The case cover 60 coupled to the upper portion of the case 50 can be opened or closed, and thus the case cover 60 is rotated about the upper portion of the case 50 to be opened, and the rotator cover 30 is separated from the upper portion of the receiving unit 20 to inject a material extracted from a human body into the receiving unit 20. Instead of this method, a material may be injected into the receiving unit 20 using the inflow tube 61 connected to the hose 62.

When a material is injected into the receiving unit 20, the rotator cover 30 is covered over the upper portion of the receiving unit 20 and the receiving unit 20 is sealed with the rotator cover 30 using the clips 35 and the cartridge is operated.

When the centrifuge operates, the container 40 should be in the coupled state. The container 40 is rotated upward with respect to the rotator 10 such that the opening 42 of the container 40 faces the outlet 32 of the stopper portion 31, and the supporting portion 33 is operated. The supporting portion 33 applies a magnetic force to the fixing portion 43 mounted in the container 40, and the container 40 is maintained in the coupled state while centrifuging is performed by the rotating rotator 10.

When the case cover 60 is opened or closed, the length of the inflow tube 61 installed in the case cover 60 can be shortened. The inflow tube 61 can be inserted into the inside of the receiving unit 20 by passing through the bearing 38 installed in the center of the rotator cover 30. The length of the inflow tube 61 can be shortened so that the bearing 38 and the inflow tube 61 do not interfere with each other while the case cover 60 is opened or closed.

While the rotator 10 is rotated, the material in the receiving unit 20 should not outflow upward. Thus a ring-shaped sealing (not shown) may be installed between the inflow tube 61 and the bearing 38.

When the driving motor 51 is operated and thus the rotator 10 starts to rotate, a centrifugal force is applied to the material inside the receiving unit 20. The vertical guiding portion 21 which is downward-closing in shape and has a gravity inclined surface and guides the material along the vertical guiding portion 21. As the centrifugal force increases, the material overcomes gravity and moves to the upper portion.

The centrifugal force inclined surface 24 of the horizontal guiding portion 25 guides the flow of the material in a horizontal direction. Accordingly, the material moved to the horizontal guiding portion 25 is guided by the centrifugal force inclined surface 24 with the effect of the centrifugal force and is converged to the convergent portion 27.

Referring to FIG. 6, when the rotator 10 is rotated at a first speed (rpm: revolution per minute) at which centrifuging is performed, a centrifugal force is exerted on the material inside the receiving unit 20, and thus the material is moved to the outermost portion of the receiving unit 20 and thus centrifuged. When the material is segregated into various layers according to specific gravity by centrifuging, layers formed of materials having high specific gravity and large fluid resistance are positioned away from the center of the rotation axis, and layers formed of materials having low specific gravity and small fluid resistance are positioned near the center of the rotation axis. Here, fluid resistance refers to the complex characteristic of a fluid which is unwilling to flow due to adhesive force, cohesive force, viscosity of a fluid, etc.

The material inside the receiving unit 20 is segregated into various layers such as free oil 74, fat 73, water 72, stem cells 71, etc., and the stem cell layer 71, which has the highest specific gravity, is positioned at the outermost edge of the receiving unit 20 and the rotator cover 30. Accordingly, the stem cell layer 71 passes through the outlet 32 of the stopper portion 31 and the opening 72 of the container 40 to flow into the container 40. The stem cell layer 71 forms a fluid layer at the outermost edge of the receiving unit 20 and the rotator cover 30, and is pressurized and adhered to a wall surface of an end of the container 40 due to the adhesive force of the stem cell layer 71 itself and the centrifugal force.

After centrifuging is performed, some layers of the centrifuged material may be discharged to the outside. This discharging operation is performed by reducing the speed of the rotation of the rotator 10 to a second speed which is a predetermined critical speed at which some of the centrifuged layers flow downward by gravity and the stem cell layer 71 remains inside the container 40. For example, when stem cells are separated from fat tissue, and the angle at which the center axis of the container 40 is inclined with respect to the rotation axis of the rotator 10 is 140 degrees, centrifugal force of 23 G (RCF) is sufficient to retain just the stem cells in the container and make the other fluid flow. Accordingly, here, the second speed can be set as 400 rpm.

Fluid layers inside of the container 40 except the stem cell layer 71 are materials having low specific gravity and fluid resistance such as the free oil layer 74, fat layer 73, and water layer 72, and thus when the speed of the rotator 10 is reduced to a pre-determined speed, the fluid layers move downward in the receiving unit 20 of the rotator 10 due to gravity. Here, a centrifugal force is applied to the fluid layers; however, since the fluid resistance is small, the centrifugal force and the force of the fluid resistance are less than gravity, and thus the fluid layers can move downward in the receiving unit 20.

When the stem cell layer 71, which is to be collected, is left inside the container 40, the operation of the supporting portion 33 is released such that the opening 42 of the container 40 is directed upward to release the coupling of the container 40 and the rotator cover 30, and then the rotator 10 is stopped. When the supporting portion 33 stops applying magnetic force, the container 40 is rotated around the pivot axis 41 by gravity and thus the location of the container 40 is changed to a release state directed downward. When the container 40 is converted into a release state, the driving motor 51 is stopped and the rotator 10 is stopped.

Before or after the rotator 10 is stopped, the material released to flow down to the receiving unit 20 may be discharged to the outside. After the rotator 10 is stopped, the container 40 in the release state is detached from the centrifuge. As described above, the stem cell layer 71 is put in the container 40, and thus no additional separation or dilution process is required to separate the stem cell layer 71 and stem cells can be easily collected.

When the amount of the stem cell layer 71 inside the container 40 is too small, the water layer 72 or the fat layer 73, etc. can flow into the container 40; however, the rate of these materials inside the container 40 is small, and materials having low fluid resistance also move down below the rotator 10 as the speed of the rotator 10 is reduced. However, material which is supposed to flow down to the receiving unit 20 such as the water layer 72 or the fat layer 73 may be adhered to the stem cell layer 72 and not move downward, and in this case, the material needs to be washed in the following manner.

Before washing the material, the other fluid layers moved to the lower portion of the rotator 10 need to be discharged to the outside through the inflow tube 61. Then a washing solution is injected into the receiving unit 20 of the rotator 10 through the inflow tube 61. After the washing solution is injected, the rotator 10 is rotated at the increased first speed, and thus the centrifuging process described above is repeated. When the centrifuging is completed, the speed of the rotator 10 is reduced to the second speed to move the water layer 72 or fat layer 73 to the lower portion of the rotator 10.

When a material to be obtained, for example, stem cells of the stem cell layer 71, remains inside the container 40 through the above-described processes, the container 40 and the rotator cover 30 are decoupled such that the opening 42 of the container 40 is directed upward, and then the rotator 10 is stopped. Before or after the rotator 10 is stopped, materials flown to the receiving unit 20 may be discharged to the outside. When the separation of the materials inside the receiving unit 20 is completed, the stem cell layer 71 is collected inside the container 40, and when the materials except the stem cell layer 71 are discharged, the operation of the supporting portion 33 is released. When the supporting portion 33 stops applying magnetic force, the container 40 is rotated around the pivot axis 41 by gravity and changed into a release state directed downward. When the container 40 is converted into a release state, the driving motor 51 is stopped and the rotator 10 is stopped.

When the container 40 is in a release state directed downward, no additional separation or dilution process for separating the stem cells is required since the stem cells are contained inside the contained 40 as described above and thus can be easily collected.

The container 40 can be coupled to the rotator cover 30 rotatably and detachably. Thus, after centrifuging is completed, the stem cells can be easily collected by detaching the container 40, which is rotated downward and put into a release state, from the rotator cover 30.

FIGS. 9 through 13 are cross-sectional views illustrating variations of horizontal cross-sections of the horizontal guiding portion of the centrifuge of FIG. 4 according to an embodiment of the present invention.

The horizontal cross-section of the horizontal guiding portion 25 of FIG. 4 according to an embodiment of the present invention is formed of two arcs coupled together. However, the form of the horizontal cross-section is not limited thereto but may be various shapes such as a star shape, a diamond shape, etc, having convergent portions.

In the embodiments illustrated in FIGS. 9 through 13, the horizontal guiding portion has convergent portions 27b, 27c, 27d, 27e, and 27f where centrifugal force is maximal, respectively. Material in the horizontal guiding portion flows along the inner surface of the horizontal guiding portion by centrifugal force, and thus the material is collected in the convergent portions 27b, 27c, 27d, 27e, and 27f. The rotator cover covering the upper portion of the receiving unit is formed corresponding to the shape of the horizontal guiding portion, and the container may be coupled to a position corresponding to the convergent portion 27b, 27c, 27d, 27e, or 27f of the rotator cover.

The centrifuge according to an embodiment of the present invention can be applied to all kinds of materials that can move downward from an inclined surface forming an inclination with respect to gravity, that is, both to liquids and solids such as liquid, powder, gel, a mixture of liquid and solid, colloid, solids that are nearly spherical.

Even when the amount of the above material is small, the material is affected by friction because the material flows downward on the inner wall surface of the container 40 and the inner wall surface of the receiving unit 20. While the rotator 10 is rotated, a centrifugal force is applied to the material in the container 40 and the receiving unit 20, and since the inner wall surface of the container 40 and the receiving unit 20 are inclined and form an inclined surface with respect to gravity, the material inside the container 40 and the receiving unit 20 is subject to both gravity and centrifugal force. As the speed of the rotator 10 is reduced and thus the centrifugal force becomes less than gravity, the material can flow downward along the inclined surface by gravity. Since resistance to the downward flow of the material exists, the point of time at which the material starts flowing downward depends on the characteristic of the material and thus may vary.

Assuming an ideal state when no friction is applied, when gravity and centrifugal force applied to the material are the same, an equilibrium point will happen, in which the material does not flow and the immobility state is maintained. However, in reality, friction, that is, resistance to the fluid exists, and thus the friction needs to be considered.

Figure 14:
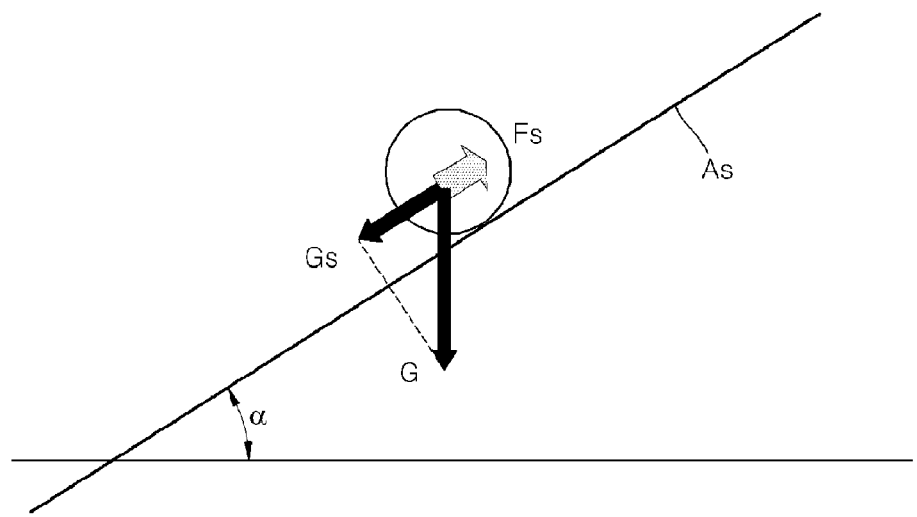
FIG. 14 is a schematic view illustrating forces applied to a material when a centrifugal force is not present in a centrifuge according to an embodiment of the present invention.

FIG. 14 is a schematic view illustrating forces applied to a material provided that a centrifugal force is not generated in a centrifuge according to an embodiment of the present invention.

In FIG. 14, the container is fixed to form an angle a with respect to a horizontal surface, thereby having an inclined surface As with respect to gravity. Here, it is assumed that the centrifuge does not rotate and thus no centrifugal force is applied. Only gravity G is applied to the material, and a component Gs of the gravity G in the direction of the inclined surface As makes the material flow downward along the inclined surface As of the container. A friction force Fs due to a fluid resistance between the material and the inclined surface As of the container is formed in an opposite direction to the flow of the material, thereby resisting the downward flow of the material.

Figure 15A:
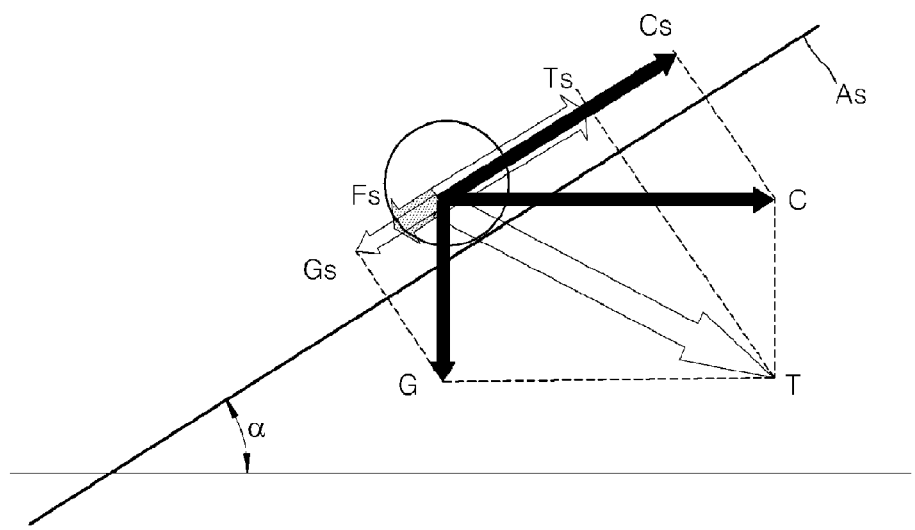
FIG. 15A schematically illustrates forces of FIG. 14 changed to a state where a large centrifugal force is applied.

FIG. 15A schematically illustrates forces of FIG. 14 changed to a state where a large centrifugal force is applied.

When the rotator is rotated, a centrifugal force C is exerted on the material. The centrifugal force C is applied horizontally, and thus a force Cs on the inclined surface As of the container makes the material flow upward. The material is pressurized toward the inclined surface As of the container due to a total force T of the centrifugal force C and gravity G. The centrifugal force C is formed to be greater than the gravity G, and thus a force Ts of the total force T applied to the material on the inclined surface. As of the container is directed upward, and as the force Ts on the inclined surface. As of the container is greater than the friction force, the material is moved upward along the inclined surface.

For the material to flow downward, the speed of the rotator needs to be further reduced so that the centrifugal force C may become smaller, or the inclined surface. As needs to be more inclined so that a force Gs on the inclined surface. As of the container may become greater. In the centrifuge according to an embodiment of the present invention, the angle of the container is fixed with respect to the rotator, and thus the inclined surface cannot be further inclined, and the inclined surface of the receiving unit is also fixed. Accordingly, the rotation speed needs to be changed.

Figure 15B:
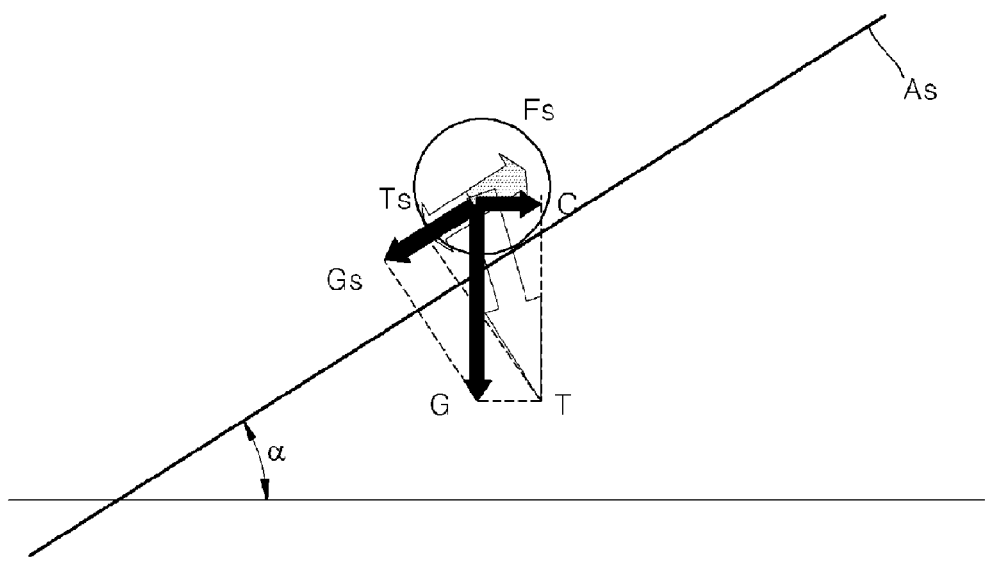
FIG. 15B schematically illustrates forces of FIG. 14 changed to another state where a small centrifugal force is applied.

FIG. 15B schematically illustrates forces of FIG. 14 changed to another state where a small centrifugal force is applied, wherein the centrifugal force is reduced.

In FIG. 15B, the speed of the rotator is reduced and thus the centrifugal force C is reduced, and a force Cs of the centrifugal force on the inclined surface As of the container became smaller. Accordingly, the force Ts of the total force T of gravity G and centrifugal force C on the inclined surface As of the container makes the material flow downward. When the speed of the rotator is reduced and the centrifugal force C becomes smaller than gravity G, the material can flow downward along the inclined surface; however, friction force Fs which is a fluid resistance between the material and the inner wall surface of the container resists the flow of the material. That is, the total force of the force of the centrifugal force C on the inclined surface and the friction force Fs are applied opposite to the force Gs on the inclined surface of gravity. Accordingly, when the force Ts on the inclined surface is greater than the friction force Fs operating as a resistance, the material can move downward.

The flow of the material downward is affected by two parameters.

First, gravity and centrifugal force are parameters concerning specific gravity. Provided that the rotator 10 is rotated at the same RPM, that is, at the same rotation speed, the greater the rotation radius, the greater the centrifugal force. Accordingly, when the rotation speed of the rotator 10 is reduced, the layer nearest to the rotation axis starts to flow down first. The greater the specific gravity of a layer is, the greater the rotation radius of the layer is. Thus, while the speed of the rotator is reduced, the material positioned at a greater rotation radius flows later than the material positioned at a smaller rotation radius. Accordingly, it is easier to obtain a material having a greater specific gravity. Also, a force that is created to move the material upward by gravity and centrifugal force is called elevating force, and the material moves upward or downward from the inclined surface depending on the size of the elevating force.

Second, friction force is a parameter concerning fluid resistance. Forces disturbing the complex flow of a fluid are determined by various parameters. Examples of the parameters are viscosity and cohesive force (surface tension) in the case of liquids, and mobility, friction in the case of solids, and adhesiveness of semisolids (gel) or mixed material. Such forces are types of frictional force. The total of all of such forces can be expressed as flow resistance or anti-gravity force.

In the centrifuge according to an embodiment of the present invention, a material having a large in specific gravity and high flow resistance can be easily separated from a material having a small specific gravity and low flow resistance. In particular, when a cell is separated, since a cell, which is an object material to be obtained, satisfies both characteristics such as a large specific gravity and high flow resistance, and thus the cell can be easily separated.

Figure 16:
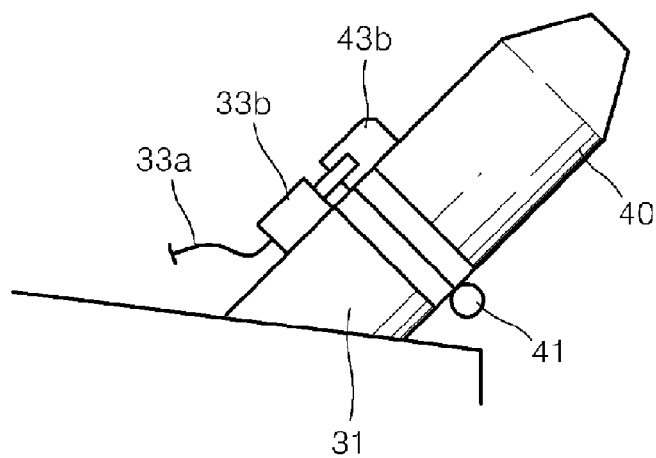
FIG. 16 is a side view illustrating a supporting structure of a container according to another embodiment of the present invention.
Figure 17:
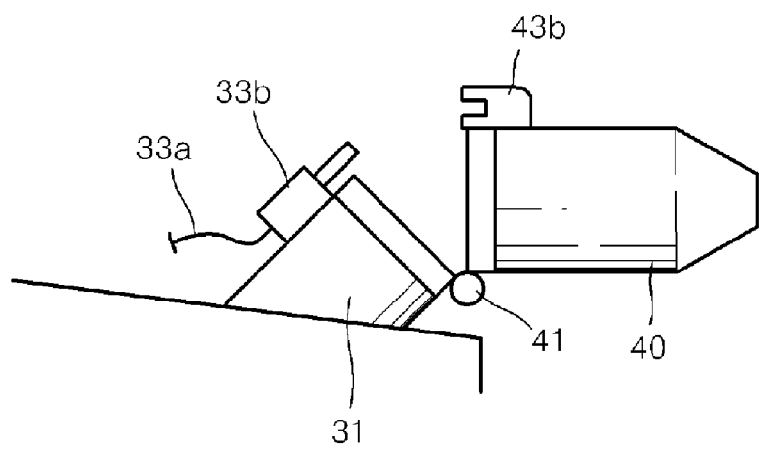
FIG. 17 is a side view of the container of FIG. 16, when the container is being rotated according to an embodiment of the present invention.
Figure 18:
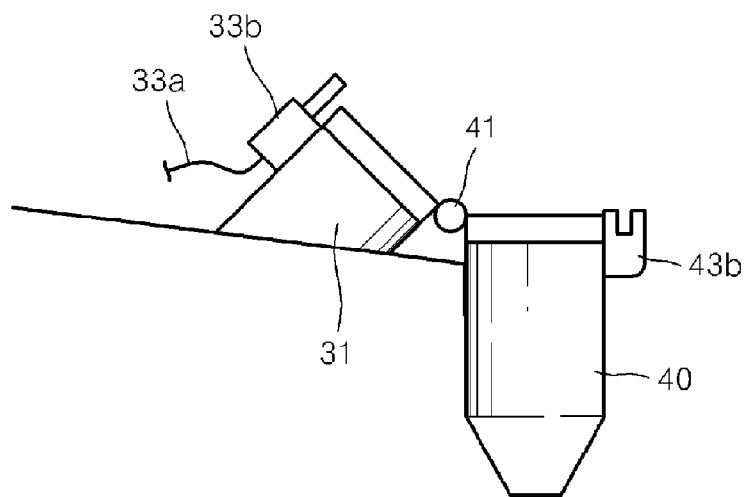
FIG. 18 is a side view of the container of FIG. 16 in a release state.

FIG. 16 is a side view illustrating a supporting structure of a container 40 according to another embodiment of the present invention; FIG. 17 is a side view of the container of FIG. 16 when the container is being rotated; and FIG. 18 is a side view of the container 40 of FIG. 16 in a release state.

Referring to the container 40 illustrated in FIG. 16, a stopper portion 31 includes a locking device 33b which is operated by external signals received through a signal line 33a. When the locking device 33b receives a signal, the locking device 33b protrudes toward the container 40 and is coupled with a coupling piece 43b attached to the container 40. When the locking device 33b is coupled to the coupling piece 43b, a coupled state, in which an opening of the container 40 is connected to an outlet of the stopper portion 31, can be maintained.

When centrifuging is completed and thus the rotator 10 is stopped, the locking device 33b is operated by external signals and is released from the coupling piece 43b. Thus the container 40 is freed from the stopper portion 31 and assumes a release state by rotating downward around a pivot axis 41 by the weight of the container 40.

In the current embodiment of the present invention, the locking device 33b is attached to the stopper portion 31 and the coupling piece 43b is attached to the container 40. However, the present invention is not limited thereto, and the positions of the locking device 33b and the coupling piece 43b may be exchanged.

Mode For Invention

Figure 19:
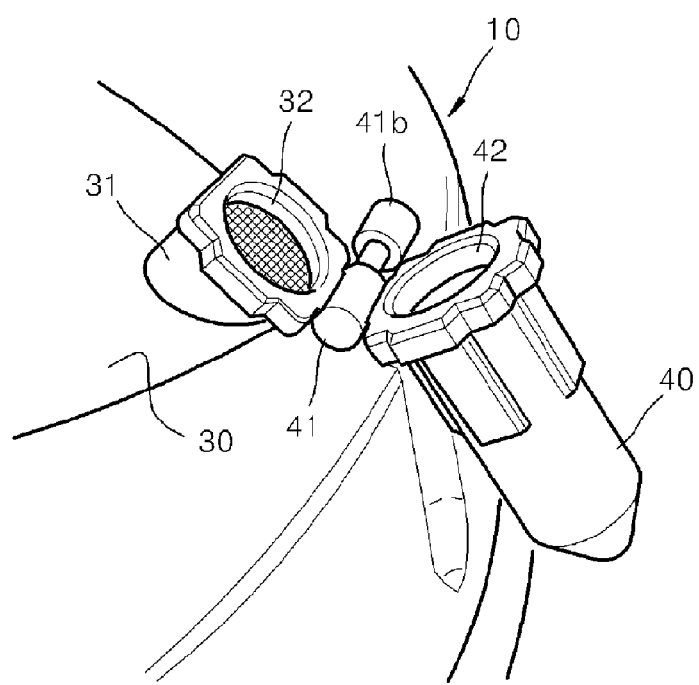
FIG. 19 is a perspective view illustrating a supporting structure of a container according to another embodiment of the present invention.

FIG. 19 is a perspective view illustrating a supporting structure of a container 40 of a centrifuge according to another embodiment of the present invention.

Referring to FIG. 19, a container 40 is rotatably coupled to a stopper portion 31, having a pivot axis 41 interposed therebetween, and a forceful driving unit is coupled to the pivot axis 41. In the current embodiment, a rotation motor 41b is used as the forceful driving unit, and other various embodiments which can generate driving force rotating the pivot axis 41 of the container 40 can be adapted. The rotation motor 41b is operated by external signals and drives the pivot axis 41 to rotate the container 40.

While centrifuging is performed, the rotation motor 41b exerts a driving force that rotates the container 40 toward the stopper portion 31 to maintain the coupled state in which the opening 42 of the container faces the outlet 32 of the stopper portion 31. When centrifuging is completed, the rotation motor 41b is driven in the opposite direction to rotate the container 40 downward.

Figure 20:
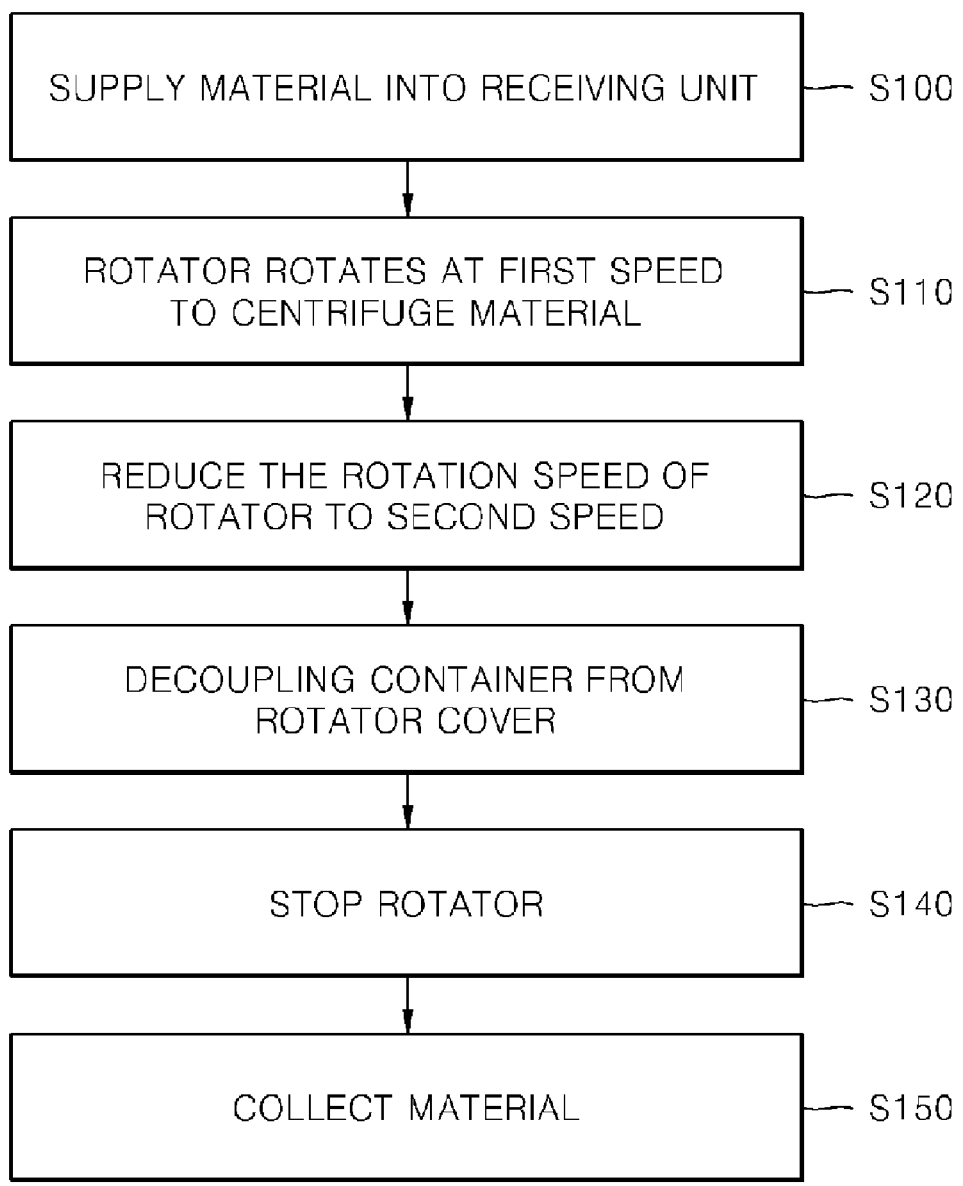
FIG. 20 is a flowchart illustrating a centrifugal method according to an embodiment of the present invention.

FIG. 20 is a flowchart illustrating a centrifugal method according to an embodiment of the present invention.

The centrifugal method according to the current embodiment of the present invention uses a rotator including a receiving unit guiding a material to move upward by centrifugal force, a rotator cover covering an upper portion of the receiving unit, and a container that is detachably coupled to the rotator cover and is connected to the receiving unit.

The centrifugal method includes providing a material into the receiving unit (S100), centrifuging the material by rotating a rotator at a first speed so that the material may move to an upper portion of the receiving unit and flow into the container (S110), reducing the rotation speed of the rotator to a second speed that is less than the first speed so that some layers of the centrifuged material flow down to the receiving unit (S 120), releasing the coupling of the rotator cover and the container so that the opening of the container may be directed upward (S 130), and stopping the rotator (S140). The centrifugal method may further include collecting the material in the container (S150) after stopping the rotator (S140).

In S120, the second speed at which the rotator is rotated may be set as a speed whereby some of the layers on the outer portion of the container among the centrifuged materials are adhered to the container and the remaining layers fall into the receiving unit due to gravity.

Also, the second speed may be set as a speed which allows 1 through 80 G of centrifugal force to be applied to the material. The second speed in the above-described range is determined based on experiments and can be adjusted so that water or fat may flow down to the receiving unit and only stem cells may be left in the container.

Figure 21:
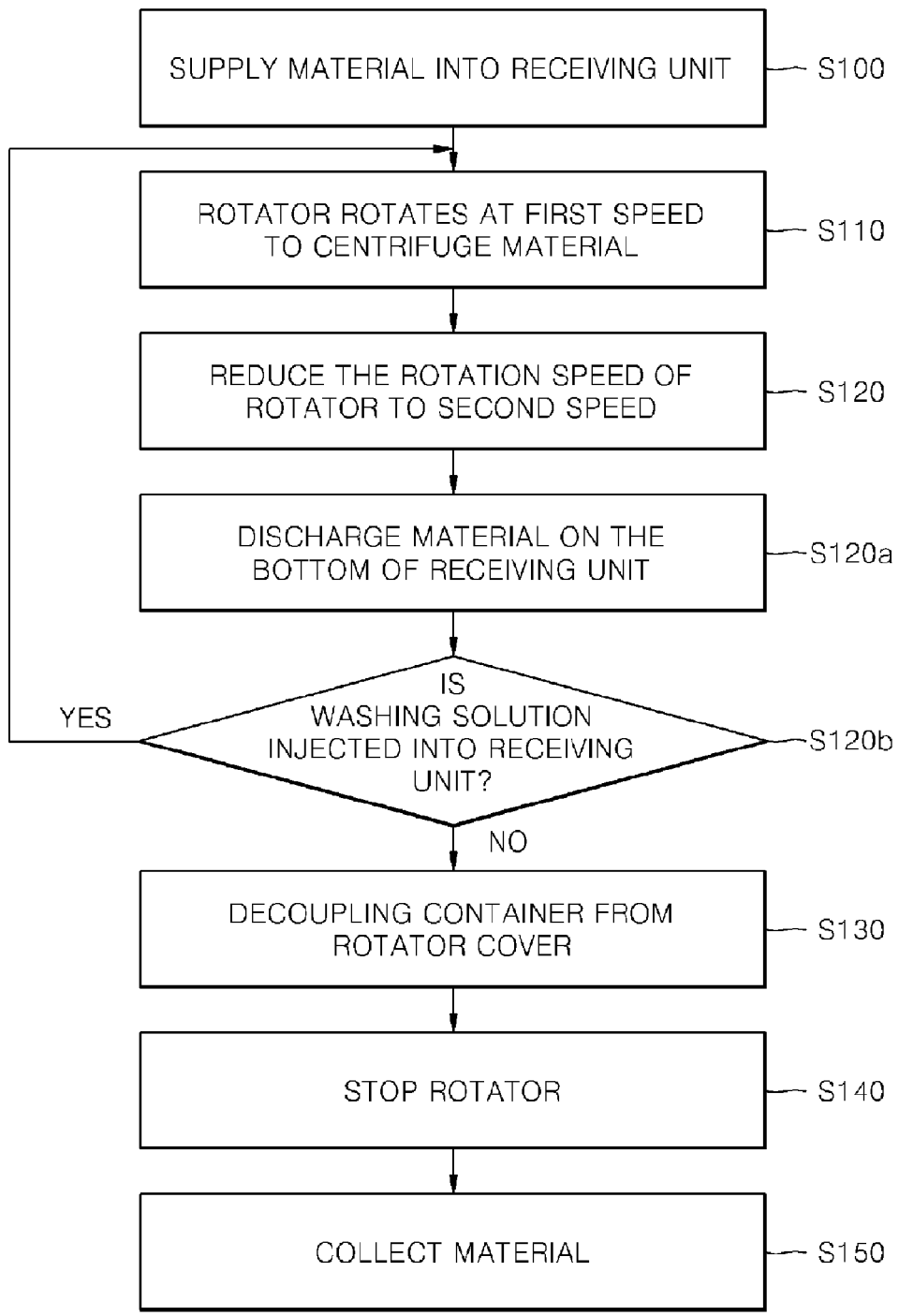
FIG. 21 is a flowchart illustrating a centrifugal method according to another embodiment of the present invention.

FIG. 21 is a flowchart illustrating a centrifugal method according to another embodiment of the present invention.

The centrifugal method according to the current embodiment of the present invention also uses a rotator including a receiving unit guiding a material to move upward by centrifugal force, a rotator cover covering an upper portion of the receiving unit, and a container that is detachably coupled to the rotator cover and is connected to the receiving unit.

The centrifugal method according to the current embodiment of the present invention illustrated in FIG. 21 further includes discharging the material received on the bottom of the receiving unit (S 120a) and injecting a washing solution into the receiving unit and repeating steps S110 through S120a (S120b).

The centrifugal method includes providing a material into the receiving unit (S100), centrifuging the material by rotating the rotator at a first speed so that the material may move to an upper portion of the receiving unit and flow into the container (S110), reducing the rotation speed of the rotator to a second speed that is less than the first speed so that some layers of the centrifuged material drops out into the receiving unit (S 120), discharging the material received on the bottom of the receiving unit through an inflow tube that passes through the rotator cover and is inserted into the receiving unit (S120a), repeating steps S110 through S120a after injecting a washing solution into the receiving unit through the inflow tube (S120b), decoupling the container from the rotator cover so that the opening of the container may be directed upward when separation of the material is completed and a washing solution is not injected (S130), and stopping the rotator (S140). The centrifugal method may further include collecting the material in the container (S 150) after stopping the rotator (S140).

The reason that operations S110 through S120a including injection of a washing solution are repeated, is to centrifuge the material again and flow layers of unnecessary materials into the receiving unit when some layers of the material to be flown into the receiving unit are mixed in layers of the materials that need to be collected separately.

While the present invention has been particularly shown and described with reference to exemplary embodiments thereof, it will be understood by those of ordinary skill in the art that various changes in form and details may be made therein without departing from the spirit and scope of the present invention as defined by the following claims.

Industrial Applicability

The present invention relates to a centrifuge and a centrifuging method of separating a fluid to which a large centrifugal force is applied and a fluid to which a smaller centrifugal force is applied by adjusting the rotation speed using the principle that centrifugal force during rotation varies according to specific components of a fluid. Thus, using the centrifuge and the centrifugal method, materials can be centrifuged and layers of the materials can be classified and collected accurately and easily.

The invention claimed is:

1. A centrifuge comprising:
 a rotator comprising a receiving unit receiving materials and guiding the materials to move upward by centrifugal force to an upper portion of the receiving unit, and a rotator cover covering the upper portion of the receiving unit; and
 a container that is coupled to the rotator cover to be connected to the receiving unit and that receives the materials moved upward along the receiving unit,
 wherein the receiving unit comprises a vertical guiding portion whose horizontal cross-section becomes reduced downwardly such that the materials received in the receiving unit flow upward by centrifugal force,
 wherein the receiving unit further comprises a horizontal guiding portion that is inclined upward from an upper end of the vertical guiding portion and extended to the outside, and
 the horizontal guiding portion comprises at least one convergent portion where the centrifugal force is maximal such that the materials moved upward from the vertical guiding portion move along an inner wall of the horizontal guiding portion and converge into the convergent portion by centrifugal force.

2. The centrifuge of claim 1, wherein a horizontal cross-section of the horizontal guiding portion is formed of two arcs that are coupled together to be curved outwardly.

3. The centrifuge of claim 1, wherein the vertical guiding portion is formed of an inverted conical shape.

4. The centrifuge of claim 1, wherein the inner wall of the vertical guiding portion is curved inwardly.

5. The centrifuge of claim 1, wherein a surface of the receiving unit is coated to reduce surface resistance against the flow of the materials.

6. The centrifuge of claim 1, wherein the rotator cover comprises a stopper portion that is connected to the receiving unit and opened to an upper portion of the rotator cover, and the container is rotatably coupled to the stopper portion, and the container is rotated between a coupled state, in which an opening of the container faces the stopper portion and is connected to the receiving unit, and a release state, in which the opening of the container is detached from the stopper portion.

7. The centrifuge of claim 6, wherein the stopper portion is disposed to correspond to the convergent portion of the horizontal guiding portion.

8. The centrifuge of claim 7, wherein the stopper portion supports the container such that the angle of the center axis of the container with respect to the rotation axis of the rotator is maintained above 90 degrees and below 180 degrees.

9. The centrifuge of claim 8, wherein the stopper portion comprises a supporting portion supporting the container in a coupled state by applying a magnetic force to the container.

10. The centrifuge of claim 9, wherein, after a portion of the centrifuged material has flown down to the receiving unit with a reduced rotation speed of the rotator, the container is converted into the release state by the supporting portion exerting opposite magnetic force or releasing magnetic force, and the container is rotated downward by gravity and centrifugal force so that the angle of the center axis of the container with respect to the rotation axis of the rotator is less than 90 degrees.

11. The centrifuge of claim 8, wherein a coupling piece and a locking device which is operated by external signals to be coupled to the coupling piece and supports the container in the coupled state, are installed between the stopper portion and the container.

12. The centrifuge of claim 11, wherein, after a portion of the centrifuged material has flown down to the receiving unit with a reduced rotation speed of the rotator, the container is converted into the release state by releasing the coupling of the locking device to the coupling piece, and the container is rotated downward by gravity and centrifugal force so that the angle of the center axis of the container with respect to the rotation axis of the rotator may be less than 90 degrees.

13. The centrifuge of claim 8, wherein the container is rotatably coupled to the stopper portion by a pivot axis disposed there between, and the pivot axis is driven by a forceful driving unit operated by external signals.

14. The centrifuge of claim 7, wherein the centrifuge further comprises a case surrounding the rotator, and a first magnetic body is installed in the case, and a second magnetic body is installed in an outer portion of the rotator, and while the rotator is rotated, the rotator and the case are maintained at a predetermined distance from each other by repulsive force between the first magnetic body and the second magnetic body.

15. The centrifuge of claim 14, further comprising:
a case cover that is coupled to the case to cover the upper portion of the rotator; and
an inflow tube that passes through the case cover and the rotator cover from the outside and is inserted into the receiving unit of the rotator, and that discharges the material received in the receiving unit to the outside or injects an external material into the receiving unit.

16. A method of centrifuging using a rotator comprising:
a receiving unit guiding a material to move upward by centrifugal force; a rotator cover covering an upper portion of the receiving unit; and
a container that is detachably coupled to the rotator cover and connected to the receiving unit, the method comprising:
(a) supplying a material to the receiving unit;
(b) centrifuging the material by rotating the rotator at a first speed such that the material moves to an upper portion of the receiving unit and flows into the container;
(c) reducing the rotation speed of the rotator to a second speed that is lower than the first speed such that some layers of the centrifuged material flow down into to the receiving unit;
(d) decoupling the container from the rotator cover such that an opening of the container is directed upward; and
(e) stopping the rotator.

17. The method of claim 16, wherein (c) further comprises discharging the material received in the receiving unit using the inflow tube that passes through the rotator cover and is connected into the receiving unit of the rotator, after the rotation speed of the rotator is reduced to the second speed.

18. The method of claim 17, further comprising injecting a washing solution into the receiving unit through the inflow tube after discharging the material received in the receiving unit, and repeating (b) and (c).

19. The method of claim 18, wherein the second speed is set as a speed creating a centrifugal force which facilitates to attach an outermost layer, which is segregated by centrifuge, to the container and makes the other layers flow down to the receiving unit by gravity.

20. The method of claim 18, wherein the second speed is set whereby 1 through 80 G of centrifugal force is applied to the material.

* * * * *